US010066064B2

(12) United States Patent
Funk et al.

(10) Patent No.: US 10,066,064 B2
(45) Date of Patent: Sep. 4, 2018

(54) PROCESS FOR REMOISTURIZING SURFACE-POSTCROSSLINKED WATER-ABSORBING POLYMER PARTICLES

(75) Inventors: Rüdiger Funk, Niedernhausen (DE); Jürgen Schröder, Ludwigshafen (DE); Thomas Pfeiffer, Boehl-Iggelheim (DE); Matthias Weismantel, Jossgrund-Oberndorf (DE)

(73) Assignee: BASF SE, Ludwigshafen (DE)

( * ) Notice: Subject to any disclaimer, the term of this patent is extended or adjusted under 35 U.S.C. 154(b) by 878 days.

(21) Appl. No.: 13/498,199

(22) PCT Filed: Oct. 5, 2010

(86) PCT No.: PCT/EP2010/064817
§ 371 (c)(1),
(2), (4) Date: Mar. 26, 2012

(87) PCT Pub. No.: WO2011/042429
PCT Pub. Date: Apr. 14, 2011

(65) Prior Publication Data
US 2012/0184684 A1    Jul. 19, 2012

Related U.S. Application Data

(60) Provisional application No. 61/250,036, filed on Oct. 9, 2009.

(51) Int. Cl.
*C08J 3/24*     (2006.01)
*A61L 15/22*   (2006.01)
*A61L 15/60*   (2006.01)
*C08F 6/26*    (2006.01)

(52) U.S. Cl.
CPC ............... *C08J 3/245* (2013.01); *A61L 15/22* (2013.01); *A61L 15/60* (2013.01); *C08F 6/26* (2013.01); *A61L 2400/18* (2013.01); *C08J 2300/14* (2013.01)

(58) Field of Classification Search
USPC ............................ 406/197; 525/344; 417/55
See application file for complete search history.

(56) References Cited

U.S. PATENT DOCUMENTS

| 2005/0013992 A1 | 1/2005 | Azad et al. |
| 2005/0222344 A1 | 10/2005 | Kondo et al. |
| 2009/0022603 A1 | 1/2009 | Feise et al. |
| 2009/0060660 A1 | 3/2009 | Funk et al. |
| 2009/0060661 A1 * | 3/2009 | Feise et al. .................... 406/197 |

FOREIGN PATENT DOCUMENTS

| EP | 0 780 424 A1 | 6/1997 |
| EP | 2 135 669 A1 | 12/2009 |
| WO | WO98/49221 | * 11/1998 |
| WO | WO-98/49221 A1 | 11/1998 |
| WO | WO-2007/104657 A2 | 9/2007 |
| WO | WO-2007/104673 A2 | 9/2007 |
| WO | WO-2007/104676 A1 | 9/2007 |

OTHER PUBLICATIONS

Buchholz, Fredric L., et al. *Modern Superabsorbent Polymer Technology*, "Solution Polymerization: Unit Operations and Their Effect on Product Quality." New York: John Wiley & Sons, Inc., 1998, pp. 71-103.
International Search Report in International Application No. PCT/EP2010/064817, dated Jan. 4, 2011 (English translation).

* cited by examiner

*Primary Examiner* — Monique Peets
(74) *Attorney, Agent, or Firm* — Marshall, Gerstein & Borun LLP

(57) ABSTRACT

A process for producing water-absorbing polymer particles, wherein surface postcrosslinked water-absorbing polymer particles are remoisturized and delivered pneumatically, and wherein the time between remoisturization and pneumatic delivery is less than one hour.

13 Claims, No Drawings

PROCESS FOR REMOISTURIZING SURFACE-POSTCROSSLINKED WATER-ABSORBING POLYMER PARTICLES

CROSS-REFERENCE TO RELATED APPLICATIONS

This is the U.S. national phase of International Application No. PCT/EP2010/064817, filed Oct. 5, 2010, which claims the benefit of U.S. provisional Application No. 61/250,036, filed Oct. 9, 2009, incorporated herein by reference in its entirety.

The present invention relates to a process for producing water-absorbing polymer particles, wherein surface postcrosslinked water-absorbing polymer particles are remoisturized and delivered pneumatically, and wherein the time between remoisturization and pneumatic delivery is less than one hour.

Water-absorbing polymer particles are used to produce diapers, tampons, sanitary napkins and other hygiene articles, but also as water-retaining agents in market gardening. The water-absorbing polymer particles are also referred to as superabsorbents.

The production of water-absorbing polymer particles is described in the monograph "Modern Superabsorbent Polymer Technology", F. L. Buchholz and A. T. Graham, Wiley-VCH, 1998, pages 71 to 103.

The properties of the water-absorbing polymer particles can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the application properties, for example permeability of the swollen gel bed (SFC) in the diaper and absorption under a pressure of 49.2 g/cm$^2$ (AUL0.7 psi), water-absorbing polymer particles are generally surface postcrosslinked. This increases the degree of crosslinking of the particle surface, which allows the absorption under a pressure of 49.2 g/cm$^2$ (AUL0.7 psi) and the centrifuge retention capacity (CRC) to be at least partly decoupled. This surface postcrosslinking can be performed in the aqueous gel phase. Preferably, however, dried, ground and screened-off polymer particles (base polymer) are surface coated with a surface postcrosslinker and thermally surface postcrosslinked. Crosslinkers suitable for this purpose are compounds which can form covalent bonds with at least two carboxylate groups of the water-absorbing polymer particles.

After the thermal surface postcrosslinking, the water-absorbing polymer particles often have a moisture content of less than 1% by weight. This increases the tendency of the polymer particles to static charging. The static charging of the polymer particles influences the dosage accuracy, for example in diaper production. This problem is typically solved by establishing a defined moisture content by adding water or aqueous solutions (remoisturizing).

Processes for remoisturizing are disclosed, for example, in WO 98/49221 A1 and EP 0 780 424 A1.

Water-absorbing polymer particles can be transported by means of pneumatic delivery systems.

Processes for pneumatic delivery are described, for example, in WO 2007/104657 A2, WO 2007/104673 A2 and WO 2007/104676 A1.

It was an object of the present invention to provide an improved process for producing water-absorbing polymer particles, especially to prevent and/or improve the removal of excessively small polymer particles.

The object was achieved by a process for producing water-absorbing polymer particles by polymerizing a monomer solution or suspension comprising a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a) and
e) optionally one or more water-soluble polymers, comprising drying, grinding, classifying and surface postcrosslinking, in which i) the surface postcrosslinked polymer particles are remoisturized,
ii) the remoisturized polymer particles are pneumatically delivered, and
iii) optionally, the remoisturized polymer particles are classified, wherein the time between the remoisturization i) and the pneumatic delivery ii) is less than one hour.

The remoisturization i) is typically performed by adding an aqueous liquid in suitable mixing units. Suitable aqueous liquids are water, aqueous solutions and aqueous dispersions. It is advantageous to use mixers with high-speed mixing tools, since this minimizes the tendency of the water-absorbing polymer particles to form lumps. Further parameters which influence the tendency to form lumps are the temperature of the water-absorbing polymer particles and the ionic strength of the aqueous solution used for remoisturization. The tendency to form lumps decreases with rising temperature and rising ionic strength.

The temperature of the water-absorbing polymer particles supplied to the remoisturization i) is therefore preferably from 40 to 80° C., more preferably from 45 to 75° C., most preferably from 50 to 70° C.

The mixers usable for remoisturization i) are not subject to any restriction. Preference is given to using mixers with rotating mixing tools. According to the position of the axis of rotation with respect to the product flow direction, the mixers with rotating mixing tools are divided into vertical mixers and horizontal mixers. It is advantageous to use horizontal mixers for remoisturization.

Suitable horizontal mixers with moving mixing tools are, for example, screw mixers, disk mixers, paddle mixers, helical ribbon mixers and continuous flow mixers. The aqueous liquid can be sprayed on either in high-speed mixers or in mixers with low stirrer speed. A preferred horizontal mixer is the continuous flow mixer. Suitable continuous flow mixers are obtainable, for example, from Gebrüder Ruberg GmbH & Co KG, Nieheim, Germany.

The inner wall of the horizontal mixer has, with respect to water, a contact angle of preferably less than 80°, more preferably of less than 65°, most preferably of less than 50°. The contact angle is a measure of the wetting behavior and is measured to DIN 53900.

It is advantageous to use horizontal mixers whose inner wall which is in contact with the product is made of a stainless steel. Stainless steels typically have a chromium content of 10.5 to 13% by weight of chromium. The high chromium content leads to a protective passivation composed of chromium dioxide on the steel surface. Further alloy constituents increase the corrosion resistance and improve the mechanical properties.

Particularly suitable steels are austenitic steels with, for example, at least 0.08% by weight of carbon. Advantageously, the austenitic steels comprise, as well as iron, carbon, chromium, nickel and optionally molybdenum, further alloy constituents, preferably niobium or titanium.

The preferred stainless steels are steels with materials number 1.45xx according to DIN EN 10020, where xx may be a natural number between 0 and 99. Particularly preferred materials are the steels with materials numbers 1.4541 and 1.4571, especially steel with materials number 1.4571.

Advantageously, the inner wall of the horizontal mixer which is in contact with the product is polished. Polished stainless steel surfaces have a lower roughness and a lower contact angle with respect to water than matt or roughened steel surfaces.

The residence time in the horizontal mixer is preferably from 1 to 180 minutes, more preferably from 2 to 60 minutes, most preferably from 5 to 20 minutes.

The peripheral speed of the mixing tools in the horizontal mixer is preferably from 0.1 to 10 m/s, more preferably from 0.5 to 5 m/s, most preferably from 0.75 to 2.5 m/s.

The surface postcrosslinked water-absorbing polymer particles are moved in the horizontal mixer at a speed which corresponds to a Froude number of preferably 0.01 to 6, more preferably 0.05 to 3, most preferably 0.1 to 0.7.

For mixers with horizontally mounted mixing tools, the Froude number is defined as follows:

$$Fr = \frac{\omega^2 r}{g}$$

where
r: radius of the mixing tool
ω: angular frequency
g: acceleration due to gravity.

The fill level of the horizontal mixer is preferably from 30 to 80%, more preferably from 40 to 75%, most preferably from 50 to 70%.

The aqueous liquid is preferably sprayed on by means of a two-substance nozzle, more preferably by means of an internally mixing two-substance nozzle.

Two-substance nozzles enable atomization into fine droplets or a spray mist. The atomization form employed is a circular or else elliptical solid or hollow cone. Two-substance nozzles may be configured with external mixing or internal mixing. In the case of the externally mixing two-substance nozzles, liquid and atomizer gas leave the nozzle head through separate orifices. They are mixed in the spray jet only after leaving the spray nozzle. This enables independent regulation of droplet size distribution and throughput over a wide range. The spray cone of the spray nozzle can be adjusted via the air cap setting. In the case of the internally mixing two-substance nozzle, liquid and atomizer gas are mixed within the spray nozzle and the biphasic mixture leaves the nozzle head through the same bore (or through a plurality of parallel bores). In the case of the internally mixing two-substance nozzle, the quantitative ratios and pressure conditions are more highly coupled than in the case of the externally mixing spray nozzle. Small changes in the throughput therefore lead to a change in the droplet size distribution. The adjustment to the desired throughput is effected through the selected cross section of the nozzle bore.

Useful atomizer gases include compressed air, gas or steam of 0.5 bar and more. The droplet size can be adjusted individually via the ratio of liquid to atomizer gas, and also gas and liquid pressure.

In a particularly preferred embodiment, the liquid in the horizontal mixer is sprayed below the product bed surface of the moving polymer particle layer, preferably at least 10 mm, more preferably at least 50 mm, most preferably at least 100 mm, i.e. the spray nozzle is immersed into the product bed.

The product bed surface is the interface which is established between the surface postcrosslinked water-absorbing polymer particles which are moved within the horizontal mixer and the blanketing atmosphere.

In the horizontal mixer, the angle between the mixer axis and the feed to the spray nozzle is preferably approx. 90°. The liquid can be supplied vertically from above. A feed obliquely from the side is likewise possible, in which case the angle relative to the vertical is preferably between 60 and 90°, more preferably between 70 and 85°, most preferably between 75 and 82.5°. The oblique arrangement of the feed enables the use of shorter feeds and hence lower mechanical stresses during the operation of the horizontal mixer.

In a particularly preferred embodiment, the spray nozzle in the horizontal mixer is below the axis of rotation and sprays in the direction of rotation. By virtue of this arrangement, the remoisturized water-absorbing polymer particles are conveyed optimally away from the spray nozzle. In combination with the oblique arrangement, it is also possible to exchange the spray nozzle during the operation of the mixer, without product escaping.

In a further preferred embodiment of the present invention, at least one spray nozzle is thermally insulated and/or trace-heated.

"Thermally insulated" means that the outer surface of the spray nozzle at least partly has a further material layer, the material of said further material layer having a lower thermal conductivity than the material of the spray nozzle. The thermal conductivity of the material of the further material layer at 20° C. is preferably less than 2 $Wm^{-1}K^{-1}$, more preferably less than 0.5 $Wm^{-1}K^{-1}$, most preferably less than 0.1 $Wm^{-1}K^{-1}$.

"Trace-heated" means that thermal energy is additionally supplied to the spray nozzle, for example by means of electrical energy or by means of a heating jacket through which a heat carrier flows. Suitable heat carriers are commercial heat carrier oils, such as Marlotherm®, steam or hot water.

A possible supply of heat via one of the feedstocks used in the mixing, i.e. surface postcrosslinked water-absorbing polymer particles or liquid to be sprayed, is not trace heating in the context of the present invention.

The temperature of the spray nozzle is preferably from 1 to 20° C., more preferably from 2 to 15° C., most preferably from 5 to 10° C., higher than the temperature of the surface postcrosslinked water-absorbing polymer particles.

In the case of a thermally insulated spray nozzle, the temperature of the liquid to be sprayed is preferably from 1 to 20° C., more preferably from 2 to 15° C., most preferably from 5 to 10° C., higher than the temperature of the surface postcrosslinked water-absorbing polymer particles. The temperature of the liquid to be sprayed corresponds approximately to the temperature of the spray nozzle.

In the case of a trace-heated and optionally thermally insulated spray nozzle, the temperature difference between the surface postcrosslinked water-absorbing polymer particles and the liquid to be sprayed on is preferably less than 20° C., preferentially less than 10° C., more preferably less than 5° C., most preferably less than 2° C.

The temperature difference between the liquid to be sprayed on and the atomizer gas is preferably less than 20° C., preferentially less than 10° C., more preferably less than 5° C., most preferably less than 2° C.

The aqueous liquids usable for remoisturization i) preferably comprise inorganic particulate substances, inorganic colloidally dissolved substances, organic polymers, cationic polymers and/or polyvalent metal cations. Suitable cationic polymers and/or polyvalent metal cations are, in a preferred embodiment, present before the remoisturization i) in the form of water-soluble salts thereof with organic or inorganic anions, and are used in the form of aqueous solutions or aqueous dispersions.

Suitable inorganic particulate substances (inorganic particles) are clay minerals such as montmorillonite, kaolinite and talc, water-insoluble sulfates such as strontium sulfate, calcium sulfate and barium sulfate, carbonates such as magnesium carbonate, potassium carbonate and calcium carbonate, salts of polyvalent metal cations such as aluminum sulfate, aluminum nitrate, aluminum chloride, potassium aluminum sulfate (potassium alum) and sodium aluminum sulfate (sodium alum), magnesium sulfate, magnesium citrate, magnesium lactate, zirconium sulfate, zirconium lactate, iron lactate, iron citrate, calcium acetate, calcium propionate, calcium citrate, calcium lactate, strontium lactate, zinc lactate, zinc sulfate, zinc citrate, aluminum lactate, aluminum acetate, aluminum formate, calcium formate, strontium formate, strontium acetate, oxides such as magnesium oxide, aluminum oxide, zinc oxide, iron(II) oxide, zirconium dioxide and titanium dioxide, water-insoluble phosphates such as magnesium phosphate, strontium phosphate, aluminum phosphate, iron phosphate, zirconium phosphate and calcium phosphate, diatomaceous earth, polysilicic acids, zeolites and activated carbons. Preference is given to using polysilicic acids which, according to the method of preparation, are distinguished between precipitated silicas and fumed silicas. Both variants are commercially available under the names Silica FK, Sipernat®, Wessalon® (precipitated silicas), or Aerosil® (fumed silicas). Also advantageous are colloidal silica solutions, in which the silica particles typically have a diameter of less than 1 μm. Such solutions are available under the name Levasil®.

However, preference is given to using water-insoluble inorganic particles, for example fumed silica, precipitated silica and water-insoluble metal phosphates. Suitable water-insoluble inorganic particles are described in DE 102 39 074 A1, and suitable water-insoluble metal phosphates in U.S. Pat. No. 6,831,122, both of which explicitly form part of the present disclosure.

In this context "water-insoluble" means a solubility in water at 23° C. of less than 1 g/100 g of water, preferably of less than 0.5 g/100 g of water, more preferably of less than 0.1 g/100 g of water, most preferably of less than 0.05 g/100 g of water.

Preferably fumed silicas and/or precipitated silicas are used as inorganic particles.

The inorganic particles have a mean particle size of preferably less than 400 μm, more preferably less than 100 μm, most preferably less than 50 μm.

When inorganic particles are used, the amount used, based on the water-absorbing polymer particles, is preferably from 0.05 to 5% by weight, more preferably from 0.1 to 1.5% by weight, most preferably from 0.3 to 1% by weight.

Suitable organic polymers are all polyfunctional amines with primary or secondary amino groups, such as polyethyleneimine, polyallylamine and polylysine. The organic polymers preferred in the process according to the invention are polyamines, such as polyvinylamine. Particularly suitable organic polymers are N-containing polymers described in DE 102 39 074 A1, which explicitly form part of the present disclosure. In a preferred embodiment, the partly hydrolyzed poly-N-vinylcarboxamides described there are used.

When organic polymers are used, the amount of organic polymer used, based on the water-absorbing polymer particles, is preferably from 0.1 to 15% by weight, more preferably from 0.5 to 10% by weight, most preferably from 1 to 5% by weight.

Suitable cationic polymers are cationic derivatives of polyacrylamides and polyquaternary amines. The anions of the cationic polymers used are all known organic and inorganic anions, preference being given to chloride, formate, acetate, propionate, malate, tartrate, citrate and lactate. The cationic polymers may, however, also be used, for example, in the form of sulfates, phosphates or carbonates, in which case sparingly water-soluble salts may form, which can be used in the form of powders or aqueous dispersions.

Polyquaternary amines are, for example, condensation products of hexamethylenediamine, dimethylamine and epichlorohydrin, condensation products of dimethylamine and epichlorohydrin, copolymers of hydroxyethylcellulose and diallyldimethylammonium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride, and addition products of epichlorohydrin onto amidoamines. In addition, it is possible to obtain polyquaternary amines by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available in a wide molecular weight range.

When cationic polymers are used, the amount of cationic polymer used, based on the water-absorbing polymer particles, is preferably from 0.1 to 15% by weight, more preferably from 0.5 to 10% by weight, most preferably from 1 to 5% by weight.

Suitable polyvalent metal cations are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate, citrate, tartrate and lactate. Aluminum sulfate, aluminum lactate and zirconium sulfate are preferred. In the presence of different diastereomers, as in the case of tartaric acid, all forms are included and can be used as anions for all polyvalent metal cations usable in accordance with the invention. The polyvalent metal cations are preferably used in the form of a solution.

Further particularly suitable polyvalent metal cations are described in WO 2005/080479 A1, which explicitly forms part of the present disclosure. It is also possible to use any desired mixtures of the soluble salts of mono- and polyvalent metal cations; for example, it is possible to prepare and use a suitable aqueous solution by dissolving lactic acid or alkali metal lactate together with aluminum sulfate. The principle can be generalized to any desired salts of polyvalent metal cations. It is also possible to use mixtures of different polyvalent metal cations or any desired mixtures of salts thereof, for example zirconium lactate and aluminum lactate, aluminum lactate and calcium lactate, zirconium lactate and calcium citrate.

Furthermore, it is possible for any desired organic and inorganic salts of monovalent cations, preferably alkali metal salts, organic acids and/or inorganic acids, additionally to be present in the solution with the polyvalent metal cations. Examples thereof are alkali metal phosphates, alkali metal sulfates, alkali metal hydrogensulfates, alkali metal dihydrogenphosphates, alkali metal hydrogencarbonates, alkali metal hydrogensulfites, and formates, acetates, lactates, propionates, tartrates, citrates, malates of the alkali metals, of ammonium and of triethanolammonium.

When polyvalent metal cations are used, the amount of polyvalent metal cation used, based on the water-absorbing polymer particles, is typically at least 0.0001% by weight, preferably from 0.005 to 5% by weight, more preferably from 0.05 to 1.5% by weight, most preferably from 0.1 to 1% by weight.

The remoisturized polymer particles are subsequently pneumatically delivered.

In principle, a distinction can be drawn between three different delivery types in pneumatic delivery.

In the case of aerial delivery and stream delivery in the region of high gas velocities, the laws of the free-flowing individual particle apply approximately. This is the classical type of pneumatic delivery. No product deposits whatsoever occur. There is essentially uniform delivery material distribution in the tube.

When the gas velocity falls, the delivery moves into the range of strand delivery, where the delivery material flows in the lower half of the tube in particular. In the upper half of the tube, there is aerial delivery.

At low gas velocities, the delivery proceeds extremely gently as dense stream delivery (plug delivery, momentum delivery) with high pressure drop.

In principle, pressure delivery can work with slower delivery rates than suction delivery, since the pressure reserves under elevated pressure are greater than under reduced pressure, and since the delivery gas density which drives the product onward increases with rising pressure.

Since delivery gas is compressible, there is no constant pressure in the delivery line, but rather a higher pressure at the start than at the end. However, this also changes the gas volume, so that, at the start, at higher pressure, slower gas velocities predominate, and, at the end, at lower pressure, higher gas velocities predominate.

H. Kalman, Powder Technology 104 (1999) 214 to 220 describes investigations of the attrition in pneumatic delivery systems. Owing to the relatively low mechanical stress, relatively low delivery rates are advantageous. According to the publication, often unnecessarily high delivery rates are, however, often selected for safety reasons in pneumatic delivery.

Excessively low delivery rates in the region of strand delivery are problematic, since stable delivery is not possible in the unstable region between dense stream delivery and strand delivery. Instead, the mechanical stresses which occur can lead to severe damage to the delivery system, up to and including pulling of the delivery lines out of the mounts.

The optimal initial gas velocity in the pneumatic delivery ii) depends upon the diameter of the delivery line. This dependence is best described with the Froude number. For pneumatic delivery, the Froude number is defined as follows:

$$Fr = \frac{v}{\sqrt{D \times g}}$$

v gas velocity
D inner diameter of the transport line
g acceleration due to gravity.

The Froude number in the pneumatic delivery ii) of water-absorbing polymer particles is preferably from 10 to 18, more preferably from 11 to 16, most preferably from 12 to 14.

At excessively low delivery rates, the pneumatic delivery ii) becomes unstable, and relatively high delivery rates increase the undesired attrition owing to rising mechanical stress.

The delivery material loading of the pneumatic delivery ii) is preferably from 0.5 to 20 kg/kg, more preferably from 1 to 10 kg/kg, most preferably from 2 to 6 kg/kg, the delivery material loading being the quotient of delivery material mass flow rate and gas mass flow rate.

In principle, the optimal initial gas velocity also increases with rising delivery material loading.

The diameter of the pipeline in which the pneumatic delivery ii) is carried out is preferably from 3 to 30 cm, more preferably from 4 to 25 cm, most preferably from 5 to 20 cm. Excessively low tube diameters lead to a higher mechanical stress as a result of the pneumatic delivery ii) and hence promote the undesired attrition. Excessively large tube diameters enable an equally undesired settling of the water-absorbing polymer particles in the delivery line.

In order to minimize mechanical stress, the number of curves in the pipeline of a pneumatic delivery system should be at a minimum, preferably fewer than 6, preferentially fewer than 5, more preferably fewer than 4, most preferably fewer than 3. A pipeline in a pneumatic delivery system is the section between the introduction unit for the water-absorbing polymer particles and the receiving vessel, i.e. the region in which the water-absorbing polymer particles are transported in the gas stream.

The time (delay time) between the remoisturization i) and the pneumatic delivery ii) is preferably less than 45 minutes, more preferably less than 30 minutes, most preferably less than 15 minutes.

The present invention is based on the finding that the water used in the remoisturization increases the elasticity of the water-absorbing polymer particles. For the elasticity of the water-absorbing polymer particles, however, only the water close to the particle surface appears to be important. At the particle surface, the water concentration, however, is at its greatest shortly after the remoisturization. With time, the water diffuses slowly from the particle surface into the particle interior and the water concentration at the particle surface falls again.

In the course of pneumatic delivery, the water-absorbing polymer particles are mechanically stressed. Elastic water-absorbing polymer particles are damaged less significantly. It is thus advantageous to pneumatically deliver water-absorbing polymer particles immediately after the remoisturization.

The remoisturized polymer particles can subsequently be classified, which removes excessively small and/or excessively large polymer particles, and they are recycled into the process.

The screening machines suitable for the classification iii) are not subject to any restriction. Preference is given to using tumbler screening machines. Suitable tumbler screening machines are obtainable, for example, from ALLGAIER Werke GmbH, Uhingen, Germany, and MINOX Siebtechnik GmbH, Offenbach/Queich, Germany.

In a tumbler screening machine, the water-absorbing polymer particles to be classified are moved over the screen in a spiral manner owing to a forced vibration. The relatively long screening distance coupled with a small screening area leads to a high sharpness of separation in the classification. The forced vibration typically has an amplitude of 0.7 to 40 mm, preferably of 1.5 to 25 mm, and a frequency of 1 to 100 Hz, preferably of 5 to 10 Hz.

The tumbler screening machines preferably have at least 2, more preferably at least 3 and most preferably at least 4 screens. Advantageously, the water-absorbing polymer particles falling down from the upper screen are deflected by a preferably funnel-shaped apparatus in the direction of the middle of the lower screen.

The mesh size of the screens is preferably in the range from 100 to 1000 µm, more preferably in the range from 150 to 850 µm, most preferably in the range from 150 to 600 µm.

The water-absorbing polymer particles preferably have a temperature during the classification of 40 to 120° C., more preferably of 45 to 100° C., most preferably of 50 to 80° C.

The classification is particularly advantageously performed continuously. The throughput of water-absorbing polymer particles is typically at least 100 kg/m²·h, preferably at least 150 kg/m²·h, preferentially at least 200 kg/m²·h, more preferably at least 250 kg/m²·h, most preferably at least 300 kg/m²·h.

A gas stream, more preferably air, preferably flows over the water-absorbing polymer particles during the classification. The gas rate is typically from 0.1 to 10 m³/h per m² of screen area, preferably from 0.5 to 5 m³/h per m² of screen area, more preferably from 1 to 3 m³/h per m² of screen area, the gas volume being measured under standard conditions (25° C. and 1 bar). The gas stream is more preferably heated slightly before entry into the screening apparatus, typically to a temperature of 40 to 120° C., preferably to a temperature of 50 to 110° C., preferentially to a temperature of 60 to 100° C., more preferably to a temperature of 65 to 90° C., most preferably to a temperature of 70 to 80° C. The water content of the gas stream is typically less than 5 g/kg, preferably less than 4.5 g/kg, preferentially less than 4 g/kg, more preferably less than 3.5 g/kg, most preferably less than 3 g/kg. A gas stream with a low water content can be obtained, for example, by condensing an appropriate amount of water out of a gas stream with higher water content by cooling.

In a preferred embodiment of the present invention, a plurality of tumbler screening machines are operated in parallel.

The tumbler screening machines are typically electrically grounded.

The time (delay time) between the remoisturization i) and the classification iii) is preferably at least 30 minutes, more preferably at least 45 minutes, most preferably at least 60 minutes.

The present invention is based on the finding that the water used in the remoisturization lowers the glass transition temperature of the water-absorbing polymer particles; the particle surface becomes tacky. At the particle surface, the water concentration, however, is at its greatest shortly after the remoisturization. With time, the water diffuses slowly from the particle surface into the particle interior and the water concentration at the particle surface falls again. The tackiness of the particle surface thus passes through a maximum.

However, the tackiness of the particle surface causes very small particles to adhere firmly to larger particles, as a result of which these adhering, very small particles can be removed by classification only with difficulty. It is therefore advantageous, after the remoisturization, still to delay the classification for a sufficient time. Within this time, some of the water diffuses into the particle surface and the tackiness of the particle surface decreases again.

In order to achieve the desired delay time between remoisturization i) and classification iii), the water-absorbing polymer particles can be stored intermediately in suitable vessels.

The production of the surface postcrosslinked polymer particles is explained in detail hereinafter:

The water-absorbing polymer particles are produced by polymerizing a monomer solution or suspension and are typically water-insoluble.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraalloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.05 to 1.5% by weight, more preferably 0.1 to 1% by weight, most preferably 0.3 to 0.6% by weight, based in each case on monomer a). With rising crosslinker content, the centrifuge retention capacity (CRC) falls and the absorption under a pressure of 21.0 g/cm$^2$ passes through a maximum.

The initiators c) used may be all compounds which generate free radicals under the polymerization conditions, for example thermal initiators, redox initiators, photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

Typically, an aqueous monomer solution is used. The water content of the monomer solution is preferably from 40 to 75% by weight, more preferably from 45 to 70% by weight, most preferably from 50 to 65% by weight. It is also possible to use monomer suspensions, i.e. monomer solutions with excess monomer a), for example sodium acrylate. With rising water content, the energy requirement in the subsequent drying rises, and, with falling water content, the heat of polymerization can only be removed inadequately.

For optimal action, the preferred polymerization inhibitors require dissolved oxygen. The monomer solution can therefore be freed of dissolved oxygen, and the polymerization inhibitor present in the monomer solution can be deactivated, before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel, which has to be comminuted in a further process step, for example in an extruder or kneader.

To improve the drying properties, the comminuted polymer gel obtained by means of a kneader can additionally be extruded.

However, it is also possible to dropletize an aqueous monomer solution and to polymerize the droplets obtained in a heated carrier gas stream. This allows the process steps of polymerization and drying to be combined, as described in WO 2008/040715 A2 and WO 2008/052971 A1.

The acid groups of the resulting polymer gels have typically been partially neutralized. Neutralization is preferably carried out at the monomer stage. This is typically done by mixing in the neutralizing agent as an aqueous solution or preferably also as a solid. The degree of neutralization is preferably from 25 to 95 mol %, more preferably from 30 to 80 mol %, most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof.

However, it is also possible to carry out neutralization after the polymerization, at the stage of the polymer gel formed in the polymerization. It is also possible to neutralize up to 40 mol %, preferably 10 to 30 mol % and more preferably 15 to 25 mol % of the acid groups before the polymerization by adding a portion of the neutralizing agent actually to the monomer solution and setting the desired final degree of neutralization only after the polymerization, at the polymer gel stage. When the polymer gel is neutralized at least partly after the polymerization, the polymer gel is preferably comminuted mechanically, for example by means of an extruder, in which case the neutralizing agent can be sprayed, sprinkled or poured on and then carefully mixed in. To this end, the gel mass obtained can be repeatedly extruded for homogenization.

The polymer gel is then preferably dried with a belt drier until the residual moisture content is preferably 0.5 to 15% by weight, more preferably 1 to 10% by weight, most preferably 2 to 8% by weight, the residual moisture content being determined by EDANA recommended test method No. WSP 230.2-05 "Moisture Content". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size (fines) are obtained. The solids content of the gel before the drying is preferably from 25 to 90% by weight, more preferably from 35 to 70% by weight, most preferably from 40 to 60% by weight. Optionally, it is, however, also possible to use a fluidized bed drier or a paddle drier for the drying operation.

Thereafter, the dried polymer gel is ground and classified, and the apparatus used for grinding may typically be single- or multistage roll mills, preferably two- or three-stage roll mills, pin mills, hammer mills or vibratory mills.

The mean particle size of the polymer particles removed as the product fraction is preferably at least 200 μm, more preferably from 250 to 600 μm, very particularly from 300 to 500 μm. The mean particle size of the product fraction may be determined by means of EDANA recommended test method No. WSP 220.2-05 "Particle Size Distribution", where the proportions by mass of the screen fractions are plotted in cumulative form and the mean particle size is determined graphically. The mean particle size here is the value of the mesh size which gives rise to a cumulative 50% by weight.

The proportion of particles with a particle size of at least 150 μm is preferably at least 90% by weight, more preferably at least 95% by weight, most preferably at least 98% by weight.

Polymer particles with too small a particle size lower the permeability (SFC). The proportion of excessively small polymer particles (fines) should therefore be small.

Excessively small polymer particles are therefore typically removed and recycled into the process. This is preferably done before, during or immediately after the polymerization, i.e. before the drying of the polymer gel. The excessively small polymer particles can be moistened with water and/or aqueous surfactant before or during the recycling.

It is also possible in later process steps to remove excessively small polymer particles, for example after the surface postcrosslinking or another coating step. In this case, the excessively small polymer particles recycled are surface postcrosslinked or coated in another way, for example with fumed silica.

When a kneading reactor is used for polymerization, the excessively small polymer particles are preferably added during the last third of the polymerization.

When the excessively small polymer particles are added at a very early stage, for example actually to the monomer solution, this lowers the centrifuge retention capacity (CRC) of the resulting water-absorbing polymer particles. However, this can be compensated, for example, by adjusting the amount of crosslinker b) used.

When the excessively small polymer particles are added at a very late stage, for example not until an apparatus connected downstream of the polymerization reactor, for example to an extruder, the excessively small polymer particles can be incorporated into the resulting polymer gel only with difficulty. Insufficiently incorporated, excessively small polymer particles are, however, detached again from the dried polymer gel during the grinding, are therefore removed again in the course of classification and increase the amount of excessively small polymer particles to be recycled.

The proportion of particles having a particle size of at most 850 μm is preferably at least 90% by weight, more preferably at least 95% by weight, most preferably at least 98% by weight.

Advantageously, the proportion of particles having a particle size of at most 600 μm is preferably at least 90% by weight, more preferably at least 95% by weight, most preferably at least 98% by weight.

Polymer particles with too great a particle size lower the swell rate. The proportion of excessively large polymer particles should therefore likewise be small.

Excessively large polymer particles are therefore typically removed and recycled into the grinding of the dried polymer gel.

To further improve the properties, the polymer particles are surface postcrosslinked. Suitable surface postcrosslinkers are compounds which comprise groups which can form covalent bonds with at least two carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidone and its derivatives, such as 2-hydroxyethyl-2-oxazolidone in DE 198 07 502 A1, bis- and poly-2-oxazolidinones in DE 198 07 992 C1, 2-oxotetrahydro-1,3-oxazine and its derivatives in DE 198 54 573 A1, N-acyl-2-oxazolidones in DE 198 54 574 A1, cyclic ureas in DE 102 04 937 A1, bicyclic amide acetals in DE 103 34 584 A1, oxetanes and cyclic ureas in EP 1 199 327 A2 and morpholine-2,3-dione and its derivatives in WO 2003/031482 A1.

Preferred surface postcrosslinkers are glycerol, ethylene carbonate, ethylene glycol diglycidyl ether, reaction products of polyamides with epichlorohydrin, and mixtures of propylene glycol and 1,4-butanediol.

Very particularly preferred surface postcrosslinkers are 2-hydroxyethyloxazolidin-2-one, oxazolidin-2-one and 1,3-propanediol.

In addition, it is also possible to use surface postcrosslinkers which comprise additional polymerizable ethylenically unsaturated groups, as described in DE 37 13 601 A1.

The amount of surface postcrosslinkers is preferably 0.001 to 2% by weight, more preferably 0.02 to 1% by weight, most preferably 0.05 to 0.2% by weight, based in each case on the polymer particles.

In a preferred embodiment of the present invention, polyvalent cations are applied to the particle surface in addition to the surface postcrosslinkers before, during or after the surface postcrosslinking.

The polyvalent cations usable in the process according to the invention are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium. Possible counterions are chloride, bromide, sulfate, hydrogensulfate, carbonate, hydrogencarbonate, nitrate, phosphate, hydrogenphosphate, dihydrogenphosphate and carboxylate, such as acetate, citrate and lactate. Aluminum sulfate and aluminum lactate are preferred. Apart from metal salts, it is also possible to use polyfunctional amines as polyvalent cations. Polyfunctional amines are compounds with at least two amino and/or ammonium groups. Preference is given, however, to using metal cations as polyvalent cations.

The amount of polyvalent cation used is, for example, 0.001 to 1.5% by weight, preferably 0.005 to 1% by weight, more preferably 0.02 to 0.8% by weight, based in each case on the polymer particles.

The surface postcrosslinking is typically performed in such a way that a solution of the surface postcrosslinker is sprayed onto the dried polymer particles. After the spraying, the polymer particles coated with surface postcrosslinker are dried thermally, and the surface postcrosslinking reaction can take place either before or during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; US) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The content of nonaqueous solvent and/or total amount of solvent can be used to adjust the penetration depth of the surface postcrosslinker into the polymer particles.

When exclusively water is used as the solvent, a surfactant is advantageously added. This improves the wetting performance and reduces the tendency to form lumps. However, preference is given to using solvent mixtures, for example isopropanol/water, 1,3-propanediol/water and propylene glycol/water, where the mixing ratio by mass is preferably from 20:80 to 40:60.

The thermal drying is preferably carried out in contact driers, more preferably paddle driers, most preferably disk driers. Suitable driers are, for example, Hosokawa Bepex® horizontal paddle driers (Hosokawa Micron GmbH; Leingarten; Germany), Hosokawa Bepex® disk driers (Hosokawa Micron GmbH; Leingarten; Germany) and Nara paddle driers (NARA Machinery Europe; Frechen; Germany). Moreover, it is also possible to use fluidized bed driers.

The drying can be effected in the mixer itself, by heating the jacket or blowing in warm air. Equally suitable is a downstream drier, for example a shelf drier, a rotary tube oven or a heatable screw. It is particularly advantageous to mix and dry in a fluidized bed drier.

Preferred drying temperatures are in the range of 100 to 250° C., preferably 120 to 220° C., more preferably 130 to 210° C., most preferably 150 to 200° C. The preferred residence time at this temperature in the reaction mixer or drier is preferably at least 10 minutes, more preferably at least 20 minutes, most preferably at least 30 minutes, and typically at most 60 minutes.

The water-absorbing polymer particles produced by the process according to the invention have a moisture content of preferably 1 to 15% by weight, more preferably 1.5 to 10% by weight, most preferably 2 to 8% by weight, the water content being determined by EDANA recommended test method No. WSP 230.2-05 "Moisture Content".

The water-absorbing polymer particles produced by the process according to the invention have a centrifuge retention capacity (CRC) of typically at least 15 g/g, preferably at least 20 g/g, preferentially at least 22 g/g, more preferably at least 24 g/g, most preferably at least 26 g/g. The centrifuge retention capacity (CRC) of the water-absorbing polymer particles is typically less than 60 g/g. The centrifuge retention capacity (CRC) is determined by EDANA recommended test method No. WSP 241.2-05 "Centrifuge Retention Capacity".

The water-absorbing polymer particles produced by the process according to the invention have an absorption under a pressure of 49.2 g/cm$^2$ of typically at least 15 g/g, preferably at least 20 g/g, preferentially at least 22 g/g, more preferably at least 24 g/g, most preferably at least 26 g/g. The absorption under a pressure of 49.2 g/cm$^2$ of the water-absorbing polymer particles is typically less than 35 g/g. The absorption under a pressure of 49.2 g/cm$^2$ is determined analogously to EDANA recommended test method No. WSP 242.2-05 "Absorption under Pressure", except that a pressure of 49.2 g/cm$^2$ is established instead of a pressure of 21.0 g/cm$^2$.

The water-absorbing polymer particles are tested by means of the test methods described below.

Methods:

The measurements should, unless stated otherwise, be carried out at an ambient temperature of 23±2° C. and a relative air humidity of 50±10%. The water-absorbing polymer particles are mixed thoroughly before the measurement.

Saline Flow Conductivity

The saline flow conductivity (SFC) of a swollen gel layer under a pressure of 0.3 psi (2070 Pa) is, as described in EP 0 640 330 A1, determined as the gel layer permeability of a swollen gel layer of water-absorbing polymer particles, the apparatus described on page 19 and in FIG. 8 in the aforementioned patent application having been modified to the effect that the glass frit (40) is not used, and the plunger (39) consists of the same polymer material as the cylinder (37) and now comprises 21 bores of equal size distributed homogeneously over the entire contact area. The procedure and evaluation of the measurement remain unchanged from EP 0 640 330 A1. The flow is detected automatically.

The saline flow conductivity (SFC) is calculated as follows:

$$SFC[cm^3 s/g]=(Fg(t=0) \times L0)/(d \times A \times WP)$$

where Fg(t=0) is the flow of NaCl solution in g/s, which is obtained using linear regression analysis of the Fg(t) data of the flow determinations by extrapolation to t=0, L0 is the thickness of the gel layer in cm, d is the density of the NaCl solution in g/cm$^3$, A is the area of the gel layer in cm$^2$, and WP is the hydrostatic pressure over the gel layer in dyn/cm$^2$.

Centrifuge Retention Capacity

The centrifuge retention capacity (CRC) is determined by EDANA recommended test method No. WSP 241.2-05 "Centrifuge Retention Capacity".

Absorption Under a Pressure of 49.2 g/cm$^2$

The absorption under a pressure of 49.2 g/cm$^2$ (AUL0.7 psi) is determined analogously to EDANA (European Disposables and Nonwovens Association) recommended test method No. WSP 242.2-05 "Absorption under Pressure", except that a pressure of 49.2 g/cm$^2$ (AUL0.7 psi) is established instead of a pressure of 21.0 g/cm$^2$ (AUL0.3 psi).

The EDANA test methods are obtainable, for example, from EDANA, Avenue Eugène Plasky 157, B-1030 Brussels, Belgium.

EXAMPLES

Example 1 (Production of the Water-Absorbing Polymer Particles)

By continuously mixing deionized water, 50% by weight sodium hydroxide solution and acrylic acid, an acrylic acid/sodium acrylate solution was prepared, such that the degree of neutralization corresponds to 71.3 mol %. The solids content of the monomer solution was 38.8% by weight.

The polyethylenically unsaturated crosslinker used was polyethylene glycol-400 diacrylate (diacrylate proceeding from a polyethylene glycol with a mean molar mass of 400 g/mol). The amount used was 2 kg of crosslinker per t of monomer solution.

To initiate the free-radical polymerization, 1.03 kg of a 0.25% by weight aqueous hydrogen peroxide solution, 3.10 kg of a 15% by weight aqueous sodium peroxodisulfate solution and 1.05 kg of a 1% by weight aqueous ascorbic acid solution were used per t of monomer solution.

The throughput of the monomer solution was 20 t/h. The reaction solution had a temperature of 23.5° C. at the feed.

The individual components were metered in the following amounts continuously into a List Contikneter continuous kneader reactor with a capacity of 6.3 m$^3$ (LIST AG, Arisdorf, Switzerland):

20 t/h of monomer solution
40 kg/h of polyethylene glycol-400 diacrylate
82.6 kg/h of hydrogen peroxide solution/sodium peroxodisulfate solution
21 kg/h of ascorbic acid solution Between the addition point for the crosslinker and the addition sites for the initiators, the monomer solution was inertized with nitrogen.

After approx. 50% of the residence time, a metered addition of fines (1000 kg/h), which were obtained from the production process by grinding and screening, to the reactor additionally took place. The residence time of the reaction mixture in the reactor was 15 minutes.

The resulting polymer gel was placed onto a belt dryer. On the belt dryer, an air/gas mixture flowed continuously around the polymer gel and dried it. The residence time in the belt dryer was 37 minutes.

The dried polymer gel was ground and screened off to a particle size fraction of 150 to 850 μm. The resulting base polymer was surface postcrosslinked.

In a Schugi Flexomix® (Hosokawa Micron B.V., Doetinchem, the Netherlands), the base polymer was coated with a surface postcrosslinker solution and then dried in a NARA paddle dryer (GMF Gouda, Waddinxveen, the Netherlands) at 190° C. for 45 minutes.

The following amounts were metered into the Schugi Flexomix®:

7.5 t/h of base polymer
270.0 kg/h of surface postcrosslinker solution

The surface postcrosslinker solution comprised 2.8% by weight of 2-hydroxyethyl-2 oxazolidone, 2.8% by weight of aluminum sulfate, 66.1% by weight of deionized water and 28.3% by weight of isopropanol.

After being dried, the surface postcrosslinked base polymer was cooled to approx. 60° C. in a NARA paddle cooler (GMF Gouda, Waddinxveen, the Netherlands).

The resulting water-absorbing polymer particles had a centrifuge retention capacity (CRC) of 28.4 g/g.

Example 2

A ProfiMixx 47 food processor (Robert Bosch GmbH; Gerlingen-Schillerhöhe; Germany) was initially charged with 220 g of water-absorbing polymer particles from example 1, which were remoisturized with 5.5 g of water while stirring (level 4; approx. 500 rpm) and stirred for a further minute. The water was sprayed on by means of a peristaltic pump at a metering rate of 5 g/min. The tube had an internal diameter of 2.54 mm.

20 g of the remoisturized water-absorbing polymer particles in each case were subjected to mechanical stress after 0, 2, 4, 6, 8, 19, 30, 60 and 120 minutes respectively. To this end, the water-absorbing polymer particles were ground in a ball mill together with 30 ceramic bodies having round caps (approx. 7.4 g each) at 150 rpm for 5 minutes.

Subsequently, the particle size distribution was measured. The percentages reported are percent by weight. The results are summarized in table 1:

TABLE 1

Remoisturization with 2.5% by weight of water and stress period of 5 minutes

| Minutes | <150 μm | 150-180 μm | 180-300 μm | 300-600 μm | 600-850 μm | >850 μm | SFC [10$^{-7}$ cm$^3$s/g] |
|---|---|---|---|---|---|---|---|
| 0 | 0.8% | 0.9% | 12.2% | 51.5% | 34.5% | 0.2% | 17 |
| 2 | 0.6% | 1.0% | 12.2% | 49.0% | 36.9% | 0.2% | 22 |
| 4 | 0.7% | 0.8% | 12.0% | 50.9% | 35.3% | 0.2% | 29 |
| 6 | 0.8% | 0.8% | 11.2% | 48.9% | 37.6% | 0.8% | 25 |
| 8 | 1.0% | 1.0% | 13.4% | 49.0% | 35.5% | 0.2% | 22 |
| 10 | 1.2% | 1.1% | 13.6% | 49.6% | 34.5% | 0.2% | 22 |
| 30 | 1.4% | 1.2% | 13.8% | 48.9% | 34.8% | 0.2% | 20 |
| 60 | 1.4% | 1.2% | 13.8% | 48.8% | 34.7% | 0.1% | 22 |
| 120 | 1.5% | 1.4% | 13.7% | 48.5% | 35.0% | 0.1% | 23 |

Example 3

The procedure was as in example 2. Instead of grinding for 5 minutes with 30 ceramic bodies, 40 ceramic bodies were used for 15 minutes.

Subsequently, the particle size distribution was measured. The percentages reported are percent by weight. The results are summarized in table 2:

TABLE 2

| | Remoisturization with 2.5% by weight of water and stress period of 15 minutes | | | | | |
|---|---|---|---|---|---|---|
| Minutes | <150 μm | 150-180 μm | 180-300 μm | 300-600 μm | 600-850 μm | >850 μm |
| 0 | 1.1% | 0.1% | 12.6% | 64.8% | 21.6% | 0.0% |
| 2 | 2.4% | 1.5% | 16.5% | 58.2% | 21.7% | 0.0% |
| 4 | 3.4% | 1.9% | 17.2% | 56.9% | 20.5% | 0.1% |
| 6 | 4.7% | 2.3% | 18.8% | 56.3% | 18.0% | 0.0% |
| 8 | 6.0% | 2.6% | 18.7% | 54.9% | 17.8% | 0.0% |
| 10 | 5.7% | 2.7% | 21.4% | 56.2% | 14.0% | 0.0% |
| 30 | 5.5% | 2.7% | 19.8% | 55.5% | 16.5% | 0.0% |
| 60 | 7.1% | 2.7% | 21.6% | 55.1% | 13.8% | 0.0% |
| 120 | 8.8% | 3.2% | 21.6% | 55.6% | 10.7% | 0.0% |

Example 4

The procedure was as in example 3. Instead of remoisturizing with 5.5 g of water, 11.0 g of water were used.

Subsequently, the particle size distribution was measured. The percentages reported are percent by weight. The results are summarized in table 3:

TABLE 3

| | Remoisturization with 5% by weight of water and stress period of 15 minutes | | | | | |
|---|---|---|---|---|---|---|
| Minutes | <150 μm | 150-180 μm | 180-300 μm | 300-600 μm | 600-850 μm | >850 μm |
| 0 | 0.6% | 0.8% | 12.1% | 55.8% | 30.7% | 0.0% |
| 2 | 0.3% | 0.5% | 8.6% | 51.4% | 39.0% | 0.3% |
| 4 | 0.5% | 0.5% | 9.0% | 52.5% | 37.4% | 0.1% |
| 6 | 1.0% | 0.9% | 13.7% | 56.9% | 27.7% | 0.0% |
| 8 | 0.9% | 0.9% | 11.8% | 52.2% | 34.3% | 0.0% |
| 10 | 0.7% | 0.8% | 11.6% | 52.7% | 34.1% | 0.1% |
| 30 | 0.8% | 1.0% | 13.7% | 60.3% | 24.4% | 0.0% |
| 60 | 1.2% | 1.3% | 15.0% | 59.1% | 23.3% | 0.1% |
| 120 | 1.6% | 1.4% | 15.7% | 56.8% | 24.7% | 0.0% |

In each of tables 1 to 3, a significant rise in small polymer particles (<150 μm) is discernible with increasing delay time between remoisturization and mechanical stress.

The invention claimed is:

1. A process for producing water-absorbing polymer particles by polymerizing a monomer solution or suspension comprising
    at least one ethylenically unsaturated monomer which bears an acid group and may be at least partly neutralized,
    at least one crosslinker,
    at least one initiator,
    optionally one or more ethylenically unsaturated monomer copolymerizable with the ethylenically unsaturated monomer which bears an acid group, and
    optionally one or more water-soluble polymer,
    then drying, grinding, classifying, and surface postcrosslinking optionally additionally using polyvalent metal cations at 130 to 210° C. to provide dried surface postcrosslinked polymer particles,
    then remoisturizing the dried surface postcrosslinked polymer particles by adding an aqueous liquid to the particles,
    then pneumatically delivering the remoisturized surface postcrosslinked polymer particles, and
    optionally, classifying the remoisturized surface postcrosslinked polymer particles,
    wherein a time between the remoisturization and the pneumatic delivery is less than one hour.

2. The process according to claim 1, wherein the water-absorbing polymer particles are surface postcrosslinked by formation of covalent bonds.

3. The process according to claim 2, wherein polyvalent metal cations have been used additionally in the surface postcrosslinking.

4. The process according to claim 1, wherein the water-absorbing polymer particles supplied to the remoisturization have a temperature of 40 to 80° C.

5. The process according to claim 1, wherein remoisturization is effected using an aqueous solution or an aqueous dispersion comprising an inorganic particulate substance, an inorganic colloidally dissolved substance, an organic polymer, a cationic polymer, and/or a salt of a polyvalent metal cation.

6. The process according to claim 1, wherein the water-absorbing polymer particles supplied to the pneumatic delivery have a temperature of 40 to 80° C.

7. The process according to claim 1, wherein an initial velocity in the pneumatic delivery corresponds to a Froude number of from 10 to 18.

8. The process according to claim 1, wherein at least 95% by weight of the water-absorbing polymer particles have a particle size of at least 150 μm.

9. The process according to claim 1, wherein at least 95% by weight of the water-absorbing polymer particles have a particle size of at most 600 μm.

10. The process according to claim 1, wherein the water-absorbing polymer particles have a centrifuge retention capacity of at least 15 g/g.

11. The process according to claim 1, wherein the time between the moisturization and the pneumatic delivery is less than 45 minutes.

12. The process according to claim 1, wherein the time between the moisturization and the pneumatic delivery is less than 30 minutes.

13. The process according to claim 1, wherein the time between the moisturization and the pneumatic delivery is less than 15 minutes.

* * * * *